United States Patent
Ji et al.

(10) Patent No.: US 9,500,628 B2
(45) Date of Patent: *Nov. 22, 2016

(54) POWER-EFFICIENT ADAPTIVE CHANNEL STATE FEEDBACK IN DISCONTINUOUS RECEPTION SCENARIOS

(71) Applicant: Apple Inc., Cupertino, CA (US)

(72) Inventors: Zhu Ji, San Jose, CA (US); Navid Damji, Cupertino, CA (US); Johnson O. Sebeni, Fremont, CA (US)

(73) Assignee: Apple Inc., Cupertino, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/484,785

(22) Filed: Sep. 12, 2014

(65) Prior Publication Data

US 2014/0376437 A1    Dec. 25, 2014

Related U.S. Application Data

(63) Continuation of application No. 13/623,908, filed on Sep. 21, 2012, now Pat. No. 8,867,448.

(Continued)

(51) Int. Cl.
*H04W 4/00* (2009.01)
*G01N 29/36* (2006.01)
*H04W 52/02* (2009.01)
*H04W 4/02* (2009.01)
*G01N 29/04* (2006.01)
*G01N 29/34* (2006.01)

(52) U.S. Cl.
CPC .............. *G01N 29/36* (2013.01); *G01N 29/04* (2013.01); *G01N 29/34* (2013.01); *H04W 4/027* (2013.01); *H04W 52/0216* (2013.01); *H04W 52/0251* (2013.01); *Y02B 60/50* (2013.01)

(58) Field of Classification Search
CPC combination set(s) only.
See application file for complete search history.

(56) References Cited

U.S. PATENT DOCUMENTS 7,499,701 B2    3/2009  Salonaho et al.
7,724,697 B2    5/2010  Dalsgaard et al.
(Continued)

FOREIGN PATENT DOCUMENTS

EP    1931062    6/2008
EP    2339883    6/2011
(Continued)

OTHER PUBLICATIONS

Office Action from Taiwanese Application from No. 102117085, mailed Oct. 27, 2014, English and Chinese versions, pp. 1-12.
(Continued)

*Primary Examiner* — Frank Duong
(74) *Attorney, Agent, or Firm* — Meyertons, Hood, Kivlin, Kowert & Goetzel, P.C.

(57) ABSTRACT

Providing adaptive channel state feedback (CSF) reports in discontinuous reception (DRX) scenarios in a power-efficient manner. The described algorithm may be able to make adaptive decisions to carry over the CSF from previous DRX cycles based on channel conditions, DRX cycle length, and/or the requirements of CSF reporting for current DRX cycle. The proposed approach can allow for more efficient power consumption related to CSF reports in DRX scenarios where new CSF reports have little or no impact to throughput.

20 Claims, 9 Drawing Sheets

Related U.S. Application Data (60) Provisional application No. 61/647,463, filed on May 15, 2012.

(56) References Cited

U.S. PATENT DOCUMENTS

| | | |
|---|---|---|
| 7,957,360 B2 | 6/2011 | Suzuki et al. |
| 8,018,855 B2 | 9/2011 | Englund et al. |
| 8,121,045 B2 | 2/2012 | Cai et al. |
| 8,457,235 B2 | 6/2013 | Ko et al. |
| 2006/0023650 A1 | 2/2006 | Dominique et al. |
| 2007/0287468 A1 | 12/2007 | Jeong et al. |
| 2008/0043677 A1 | 2/2008 | Kim et al. |
| 2008/0045228 A1 | 2/2008 | Zhang et al. |
| 2008/0069058 A1 | 3/2008 | Geng et al. |
| 2008/0165698 A1 | 7/2008 | Dalsgaard et al. |
| 2008/0268863 A1 | 10/2008 | Pedersen et al. |
| 2009/0046652 A1 | 2/2009 | Shitara et al. |
| 2009/0135787 A1 | 5/2009 | Uemura et al. |
| 2009/0207784 A1 | 8/2009 | Lee et al. |
| 2009/0262854 A1 | 10/2009 | Lee et al. |
| 2009/0279466 A1 | 11/2009 | Ji et al. |
| 2010/0002595 A1 | 1/2010 | Iwamura et al. |
| 2010/0048209 A1 | 2/2010 | Aoyama et al. |
| 2010/0091893 A1 | 4/2010 | Gorokhov |
| 2011/0077040 A1 | 3/2011 | Nammi et al. |
| 2011/0222483 A1 | 9/2011 | Yuda et al. |
| 2011/0269462 A1 | 11/2011 | Sagfors et al. |
| 2012/0020230 A1 | 1/2012 | Chen et al. |
| 2012/0033595 A1 | 2/2012 | Aoyama et al. |
| 2012/0044831 A1 | 2/2012 | Kazmi et al. |
| 2012/0093000 A1 | 4/2012 | Jeong et al. |
| 2012/0263088 A1 | 10/2012 | Terry et al. |
| 2013/0107782 A1 | 5/2013 | Anas et al. |
| 2013/0194990 A1 | 8/2013 | Banister et al. |

FOREIGN PATENT DOCUMENTS

| | | |
|---|---|---|
| GB | 2494499 | 3/2013 |
| JP | 2007-189349 | 7/2007 |
| TW | 200910806 | 3/2009 |
| WO | 2007037218 | 4/2007 |
| WO | 2012000547 | 1/2012 |

OTHER PUBLICATIONS

International Preliminary Report on Patentability from PCT/US2013/038582, mailed Nov. 27, 2014, Apple Inc., pp. 1-10.
International Preliminary Report on Patentability from PCT/US2013/038646, mailed Nov. 27, 2014, Apple Inc., pp. 1-10.
International Preliminary Report on Patentability from PCT/US2013/039098, mailed Nov. 27, 2014, Apple Inc., pp. 1-10.
International Search Report in Application No. PCT/US2013/038582 mailed Oct. 17, 2013, 14 pages.
Office Action in Taiwanese Application No. 102116913 mailed Dec. 2, 2014, 6 pages.
Ericsson, CQI Reporting with Regards to DRX Operation, May 7-11, 2007, 2 pages.
Nokia Corporation, Nokia Siemens Networks, Samsung, CQI Reporting Configuration, Aug. 18-22, 2008, 2 pages.
Office Action in Taiwanese Application No. 102116911 dated Feb. 6, 2015, 10 pages.

| CQI Index | Modulation | Code Rate x 1024 | Efficiency |
|---|---|---|---|
| | Out of Range | | |
| 0 | | | |
| 1 | QPSK | 78 | 0.1523 |
| 2 | QPSK | 120 | 0.2344 |
| 3 | QPSK | 193 | 0.3770 |
| 4 | QPSK | 308 | 0.6016 |
| 5 | QPSK | 449 | 0.8770 |
| 6 | QPSK | 602 | 1.1758 |
| 7 | 16QAM | 378 | 1.4766 |
| 8 | 16QAM | 490 | 1.9141 |
| 9 | 16QAM | 616 | 2.4063 |
| 10 | 64QAM | 466 | 2.7305 |
| 11 | 64QAM | 567 | 3.3223 |
| 12 | 64QAM | 666 | 3.9023 |
| 13 | 64QAM | 772 | 4.5234 |
| 14 | 64QAM | 873 | 5.1152 |
| 15 | 64QAM | 948 | 5.5547 |

FIG. 3

| MCS Index $I_{MCS}$ | Modulation Order $Q_m$ | TBS Index $I_{TBS}$ |
|---|---|---|
| 0 | 2 | 0 |
| 1 | 2 | 1 |
| 2 | 2 | 2 |
| 3 | 2 | 3 |
| 4 | 2 | 4 |
| 5 | 2 | 5 |
| 6 | 2 | 6 |
| 7 | 2 | 7 |
| 8 | 2 | 8 |
| 9 | 2 | 9 |
| 10 | 4 | 9 |
| 11 | 4 | 10 |
| 12 | 4 | 11 |
| 13 | 4 | 12 |
| 14 | 4 | 13 |
| 15 | 4 | 14 |
| 16 | 4 | 15 |
| 17 | 6 | 15 |
| 18 | 6 | 16 |
| 19 | 6 | 17 |
| 20 | 6 | 18 |
| 21 | 6 | 19 |
| 22 | 6 | 20 |
| 23 | 6 | 21 |
| 24 | 6 | 22 |
| 25 | 6 | 23 |
| 26 | 6 | 24 |
| 27 | 6 | 25 |
| 28 | 6 | 26 |
| 29 | 2 | Reserved |
| 30 | 4 | |
| 31 | 6 | |

POWER-EFFICIENT ADAPTIVE CHANNEL STATE FEEDBACK IN DISCONTINUOUS RECEPTION SCENARIOS

PRIORITY CLAIM

This application is a continuation of U.S. patent application Ser. No. 13/623,908, filed Sep. 21, 2012, which claims benefit of priority to U.S. Provisional Application No. 61/647,463 titled "Power-Efficient Adaptive Channel State Feedback in Discontinuous Reception Scenarios for Wireless Transceiver" and filed on May 15, 2012, whose inventors are Zhu Ji, Navid Damji, and Johnson O. Sebeni, and which are each hereby incorporated by reference in its entirety as though fully and completely set forth herein.

FIELD OF THE INVENTION

Embodiments described herein are related to the field of wireless devices, and more particularly to a system and method for adaptively generating and transmitting channel state feedback in discontinuous reception scenarios.

DESCRIPTION OF THE RELATED ART

Wireless communication systems are rapidly growing in usage. Further, wireless communication technology has evolved from voice-only communications to also include the transmission of data, such as Internet and multimedia content. Therefore, improvements are desired in wireless communication.

In order to save the power consumption and improve the battery life of wireless user equipment (UE), discontinuous reception (DRX) has been introduced in several wireless standards such as UMTS, LTE (Long-term evolution), WiMAX, etc., which powers down most of UE circuitry when there are no packets to be received or transmitted and only wakes up at specified times or intervals to listen to the network. DRX can be enabled in different network connection states, including connection mode and idle mode. In connection DRX (CDRX) mode, the UE listens to the downlink (DL) packets following a specified pattern determined by the base-station (BS). In idle DRX (IDRX) mode, the UE listens to the page from the BS to determine if it needs to reenter the network and acquire the uplink (UL) timing.

In order to fully exploit the wireless channel status for improving the throughput at wireless user equipment (UE), metrics that indicate the channel quality can be generated at the UE for the feedback to the base-station (BS). Without loss of generality, these metrics may be referred to as channel state feedback (CSF), which may include the metrics that the UE generates based on its received downlink (DL) signals, e.g., including the estimation of the spectral efficiency, the number of data layers, the pre-coding matrices in the scenarios of multiple input and multiple output (MIMO) antenna systems, etc. These CSF metrics may be critical for the BS to determine what code rates and modulation scheme should be assigned to each UE for not only maximizing the UE throughput, but also optimizing the overall throughput of the cell through scheduling.

Reporting accurate CSFs during DRX mode (especially CDRX mode) is difficult since the on-duration of the radio is limited. The on-duration of the radio is limited due to the DRX operations and also because the channel estimation needs some time to warm up in order to provide good channel estimates for CSF estimation algorithms running at the UE. To be specific, on one hand, in order to report an accurate CSF, the UE needs to wake-up before the on-duration to allow the channel estimates to converge and CSF to be carried out, especially when CSF reports are scheduled to be transmitted for the first subframe of the on-duration. On the other hand, in order to reduce the power consumption, the overhead of CDRX needs to be minimized to reduce the preparation of CDRX on-durations hence optimizing the power consumption.

The generation of CSFs by the UE is important in optimizing use of the communication channel. Therefore, improvements are desired in the generation of CSFs in wireless communication systems.

SUMMARY OF THE INVENTION

Embodiments described herein relate to a User Equipment (UE) device and associated method for providing a channel state feedback (CSF) report to a base station (BS), e.g., for each discontinuous reception (DRX) cycle. In particular, the CSF calculated from a previous DRX cycle may be leveraged (re-used or re-transmitted as a new or current CSF) under certain scenarios in order to save the extra wake-up time to calculate a new CSF. The reuse of a previously calculated CSF may also improve the CSF report if there is a hardware/design constraint on how early the UE can be waken up before CDRX.

The UE may store a prior CSF report from a prior DRX cycle. The UE may then determine the current variance existing on the channel used for communication with the base station. This estimate of the variance of the channel may then be used to determine whether to send the prior CSF report as a current CSF report, or whether to generate a new CSF report. As one example, the UE may use a threshold value to determine whether to send the prior CSF report as a current CSF report, or whether to generate a new CSF report.

For example, each DRX cycle may have a constant cycle length, and in one implementation, the UE may compare the cycle length of the DRX to a threshold value. Where cycle length is used to compare to the threshold, if the cycle length is less than the threshold amount, the UE may provide the prior CSF report from the prior DRX cycle as a current CSF report. If the cycle length is greater than the threshold amount, the UE may generate a new CSF report and provide the new CSF report as the current CSF report. The threshold value may be based on the current Doppler shift being experienced by the UE. For example, the threshold value may be decreased for higher Doppler shift values and increased for lower Doppler shift values.

As another example, the UE compares a connection characteristic to the threshold value. The connection characteristic may comprise parameters, e.g., physical layer key performance indicators such as error rate, throughput, etc. Where error rate is used, the error rate passing the threshold may include the error rate being greater than an error rate threshold value. Where throughput is used, the throughput passing the threshold may comprise either 1) the throughput being less than a throughput threshold value; or 2) a decrease in throughput being greater than a decrease in throughput threshold value.

Where the connection characteristic is used to compare to the threshold, if the connection characteristic does not pass the threshold value, the UE may provide the prior CSF report from the prior DRX cycle as a current CSF report. If the current connection passes the threshold value, the UE may generate a new CSF report and provides the new CSF report as the current CSF report.

The UE may also estimate or determine motion of the UE device, e.g., based on a calculated Doppler shift, and may use this estimation of motion to determine whether or note to provide a prior or new CSF report.

The UE may also store the new CSF report as the prior CSF report, e.g., replacing the previous prior CSF report. In some DRX environments, the UE may provide the current CSF report at a first sub-frame of the DRX on-duration.

Another embodiment, which may be combined with those above, relates to a UE device and associated method for providing a channel state feedback (CSF) report. The UE may store a prior CSF report from a prior discontinuous reception (DRX) cycle. The UE may compare a channel estimation warm-up length to a CSF report offset added to an overhead warm-up length. If the channel estimation warm-up length is less than or equal to the CSF report offset added to the overhead warm-up length, the UE may generate a new CSF report and provides the new CSF report as the CSF report. The UE may also store the new CSF report as the prior CSF report. If the channel estimation warm-up length is greater than the CSF report offset added to the overhead warm-up length, the UE may determine whether to generate a new CSF report and then either provides the prior CSF report or generates and provides the new CSF report based on the determination.

BRIEF DESCRIPTION OF THE DRAWINGS

A better understanding of the present invention can be obtained when the following detailed description of the embodiments is considered in conjunction with the following drawings.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE EMBODIMENTS

Acronyms

The following acronyms are used in the present Provisional Patent Application:

BLER: Block Error Rate (same as Packet Error Rate)
BER: Bit Error Rate
CRC: Cyclic Redundancy Check
DL: Downlink
PER: Packet Error Rate
SINR: Signal to Interference-and-Noise Ratio
SIR: Signal to Interference Ratio
SNR: Signal to Noise Ratio
Tx: Transmission
UE: User Equipment
UL: Uplink
UMTS: Universal Mobile Telecommunication System

Terms

The following is a glossary of terms used in the present application:

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may comprise other types of memory as well or combinations thereof. In addition, the memory medium may be located in a first computer system in which the programs are executed, or may be located in a second different computer system which connects to the first computer system over a network, such as the Internet. In the latter instance, the second computer system may provide program instructions to the first computer system for execution. The term "memory medium" may include two or more memory mediums which may reside in different locations, e.g., in different computer systems that are connected over a network.

Carrier Medium—a memory medium as described above, as well as a physical transmission medium, such as a bus, network, and/or other physical transmission medium that conveys signals such as electrical, electromagnetic, or digital signals.

Programmable Hardware Element—includes various hardware devices comprising multiple programmable function blocks connected via a programmable interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Computer System (or Computer)—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

User Equipment (UE) (or "UE Device")—any of various types of computer systems devices which are mobile or portable and which performs wireless communications. Examples of UE devices include mobile telephones or smart phones (e.g., iPhone™, Android™-based phones), portable gaming devices (e.g., Nintendo DS™, PlayStation Portable™, Gameboy Advance™, iPhone™), laptops, PDAs, portable Internet devices, music players, data storage devices, or other handheld devices, etc. In general, the term "UE" or "UE device" can be broadly defined to encompass any electronic, computing, and/or telecommunications device (or combination of devices) which is easily transported by a user and capable of wireless communication.

Base Station (BS)—The term "Base Station" has the full breadth of its ordinary meaning, and at least includes a wireless communication station installed at a fixed location and used to communicate as part of a wireless telephone system or radio system.

Processing Element—refers to various elements or combinations of elements. Processing elements include, for example, circuits such as an ASIC (Application Specific Integrated Circuit), portions or circuits of individual processor cores, entire processor cores, individual processors, programmable hardware devices such as a field programmable gate array (FPGA), and/or larger portions of systems that include multiple processors.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Figure 1A:
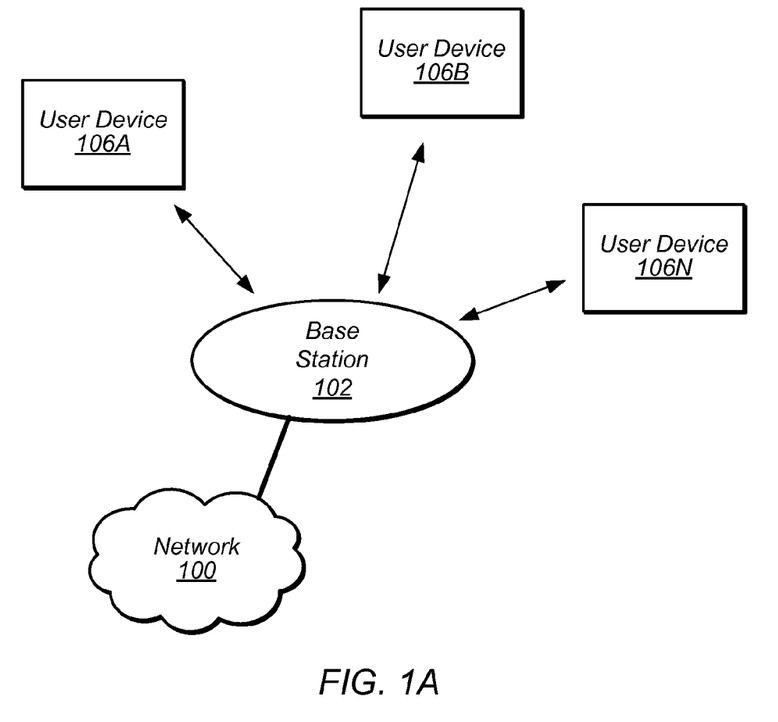
FIG. 1A illustrates an exemplary (and simplified) wireless communication system.
Figure 1B:
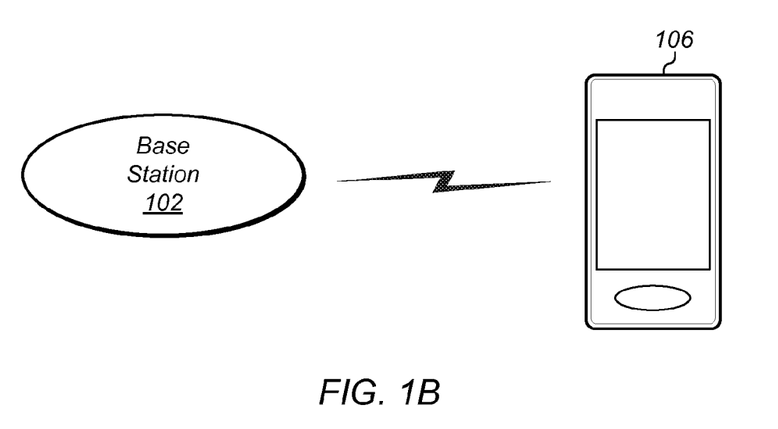
FIG. 1B illustrates a base station 102 in communication with user equipment 106.

FIGS. 1A and 1B—Communication System

FIG. 1A illustrates an exemplary (and simplified) wireless communication system. It is noted that the system of FIG. 1A is merely one example of a possible system, and embodiments of the invention may be implemented in any of various systems, as desired.

As shown, the exemplary wireless communication system includes a base station 102 which communicates over a transmission medium with one or more User Equipment (UE) (or "UE devices") 106A through 106N.

The base station 102 may be a base transceiver station (BTS) or cell site, and may include hardware that enables wireless communication with the UEs 106A through 106N. The base station 102 may also be equipped to communicate with a network 100. Thus, the base station 102 may facilitate communication between the UEs 106 and/or between the UEs 106 and the network 100. The communication area (or coverage area) of the base station may be referred to as a "cell." The base station 102 and the UEs 106 may be configured to communicate over the transmission medium using any of various wireless communication technologies such as GSM, CDMA, WLL, WAN, WiFi, WiMAX, etc.

FIG. 1B illustrates UE 106 (e.g., one of the devices 106A through 106N) in communication with the base station 102. The UE 106 may be a device with wireless network connectivity such as a mobile phone, a hand-held device, a computer or a tablet, or virtually any type of wireless device. The UE 106 may include a processor that is configured to execute program instructions stored in memory. The UE 106 may perform any of the embodiments described herein by executing such stored instructions. In some embodiments, the UE 106 may include a programmable hardware element such as an FPGA (field-programmable gate array) that is configured to perform any of the method embodiments described herein, or any portion of any of the method embodiments described herein.

In some embodiments, the UE 106 may be configured to generate channel state feedback (CSF) reports that are provided back to the base station 102. The base station 102 may use these CSF reports to adjust its communications with the respective UE 106, or possibly other UEs 106. For example, in one embodiment the base station 102 may receive and utilize CSFs from multiple UEs 106 to adjust its communication scheduling among the various UEs within its coverage area (or cell).

User equipment (UE) 106 may use a CSF report (which may be referred to as simply "CSF" herein) generation method as described herein to determine the CSF that is fed back to the base station (BS).

Figure 2:
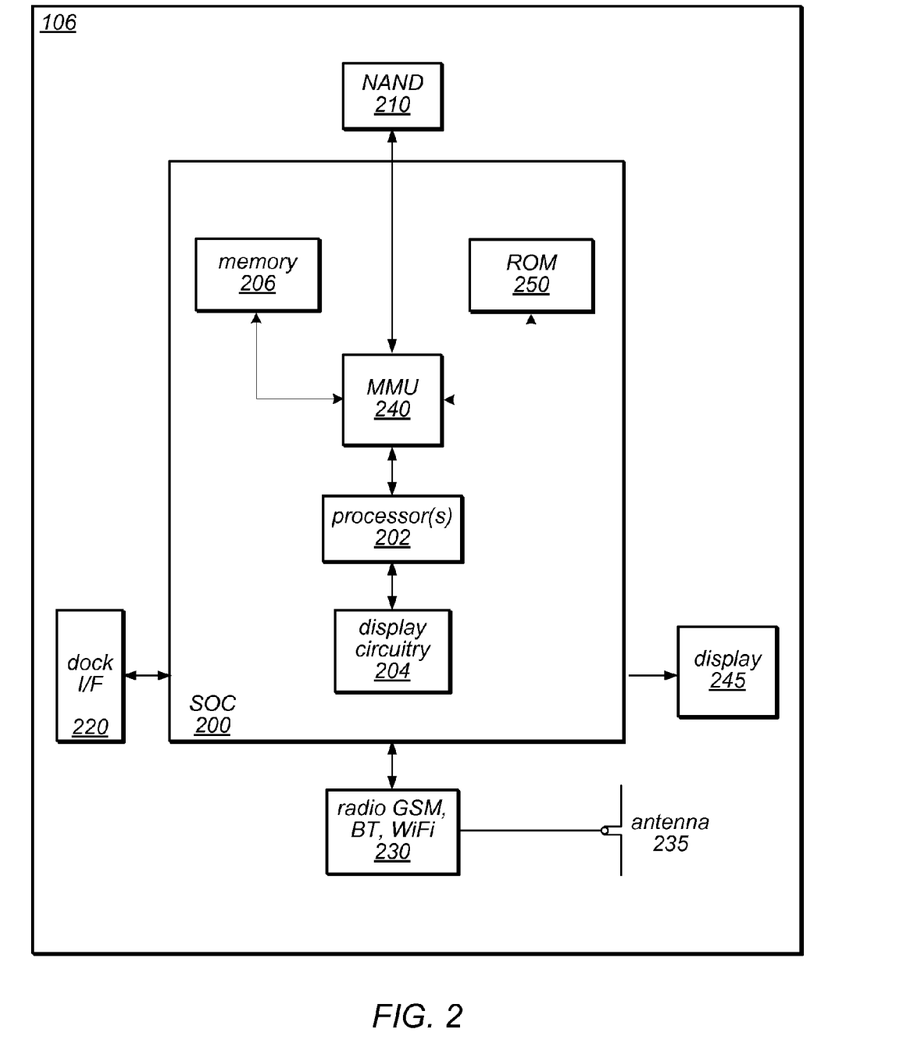
FIG. 2 illustrates an exemplary block diagram of a UE 106, according to one embodiment.

FIG. 2—Exemplary Block Diagram of a UE

FIG. 2 illustrates an exemplary block diagram of a UE 106. As shown, the UE 106 may include a system on chip (SOC) 200, which may include portions for various purposes. For example, as shown, the SOC 200 may include processor(s) 202 which may execute program instructions for the UE 106 and display circuitry 204 which may perform graphics processing and provide display signals to the display 245. The processor(s) 202 may also be coupled to memory management unit (MMU) 240, which may be configured to receive addresses from the processor(s) 202 and translate those addresses to locations in memory (e.g., memory 206, read only memory (ROM) 250, NAND flash memory 210) and/or to other circuits or devices, such as the display circuitry 204, radio 230, connector I/F 220, and/or display 245. The MMU 240 may be configured to perform memory protection and page table translation or set up. In some embodiments, the MMU 240 may be included as a portion of the processor(s) 202.

As also shown, the SOC 200 may be coupled to various other circuits of the UE 106. For example, the UE 106 may include various types of memory (e.g., including NAND flash 210), a connector interface 220 (e.g., for coupling to the computer system), the display 245, and wireless communication circuitry (e.g., for GSM, Bluetooth, WiFi, etc.) which may use antenna 235 to perform the wireless communication. As described herein, the UE 106 may include hardware and software components for generating and/or providing CQI values to a base station.

DRX

The term "DRX" refers to "discontinuous reception" and refers to a mode which powers down at least a portion of UE circuitry when there are no packets to be received or transmitted and wakes up at specified times or intervals to listen to the network. DRX is present in several wireless standards such as UMTS, LTE (Long-term evolution), WiMAX, etc. The term "DRX" is explicitly intended to at least include the full extent of its ordinary meaning, as well as similar types of modes in future standards.

In LTE, the DRX mode can be enabled in both RRC (radio resource control) CONNECTION and RRC IDLE states. In the RRC_CONNECTION state, the DRX mode may be enabled during the idle period of the DL packet arrival. In the RRC_IDLE state, the UE may be paged for DL traffic or may initiate UL traffic by requesting RRC connection with the serving BS.

The parameters for DRX cycles may be configured by the BS through different timers:

1) The DRX inactivity timer indicates the time in number of consecutive subframes to wait before enabling DRX.

2) Short DRX cycles and long DRX cycles are defined to allow the BS to adjust the DRX cycles based on the applications. In generation, a DRX short cycle timer may be defined to determine when to transition to the long DRX cycle.

3) When there is no reception of packets for an extended period of time after the successful reception of a packet, the BS may initiate RRC connection release and the UE may enter the RRC IDLE state, during which the idle DRX can be enabled.

4) The ON duration timer may be used to determine the number of frames over which the UE will read the DL control channel every DRX cycle before entering power saving mode. The allowed values are 1, 2, 3, 4, 5, 6, 8, 10, 20, 30, 40, 50, 60, 80, 100, and 200.

5) During idle DRX mode, the UE may only monitor one paging occasion (PO) per DRX cycle, which is one subframe.

CSF

The term "CSF" stands for channel state feedback and is intended to include any of various information provided by the UE to the BS indicating a state of the wireless communication channel being used. The term "CSF" is at least intended to include the full extent of its ordinary meaning In LTE, the CSF report includes the following three components: channel quality indicator (CQI), precoding matrix index (PMI), and rank indication (RI).

Figure 3:
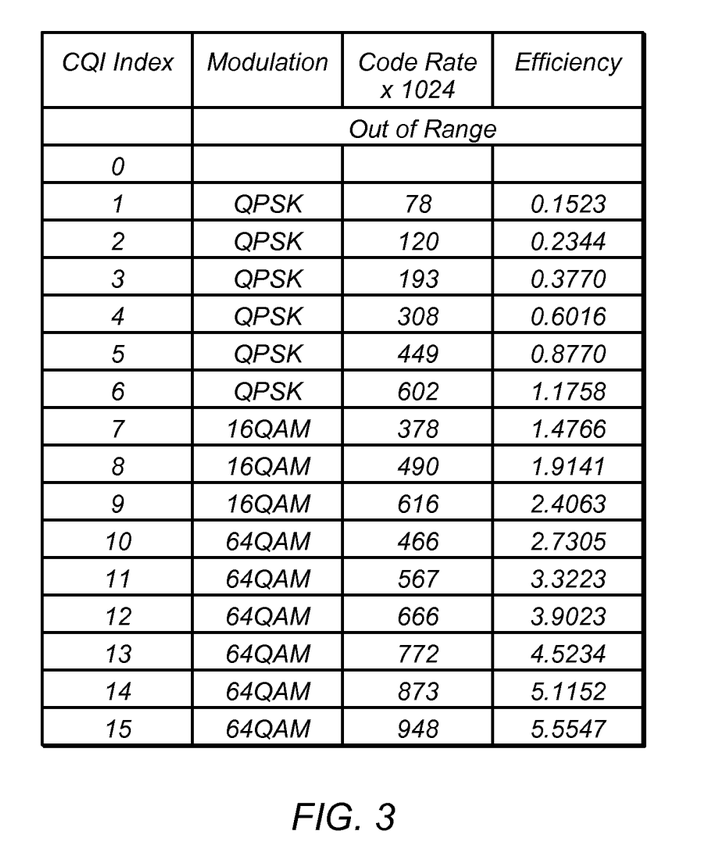
FIG. 3 illustrates an exemplary table of CQI values according to one embodiment of the invention.

Within LTE, CQI is defined as follows: Based on an unrestricted observation interval in time and frequency, the UE derives for each CQI value reported in uplink subframe n the highest CQI index between 1 and 15 in the Table shown in FIG. 3 which satisfies the following condition, or CQI index 0 if CQI index 1 does not satisfy the condition: A single PDSCH transport block with a combination of modulation scheme and transport block size corresponding to the CQI index, and occupying a group of downlink physical resource blocks termed the CQI reference resource, could be received with a transport block error probability not exceeding 0.1.

Within LTE, PMI is defined as the precoding matrix index that the UE can feedback to the BS for its selection of precoding matrix to optimize the throughput. The UE usually determines the optimal PMI based on its channel estimation and calculates the expected throughput with available hypotheses of precoding matrices.

Within LTE, RI is defined as the indicator that signals the BS the number of transmission layers the UE can support to optimize throughput.

Figure 4:
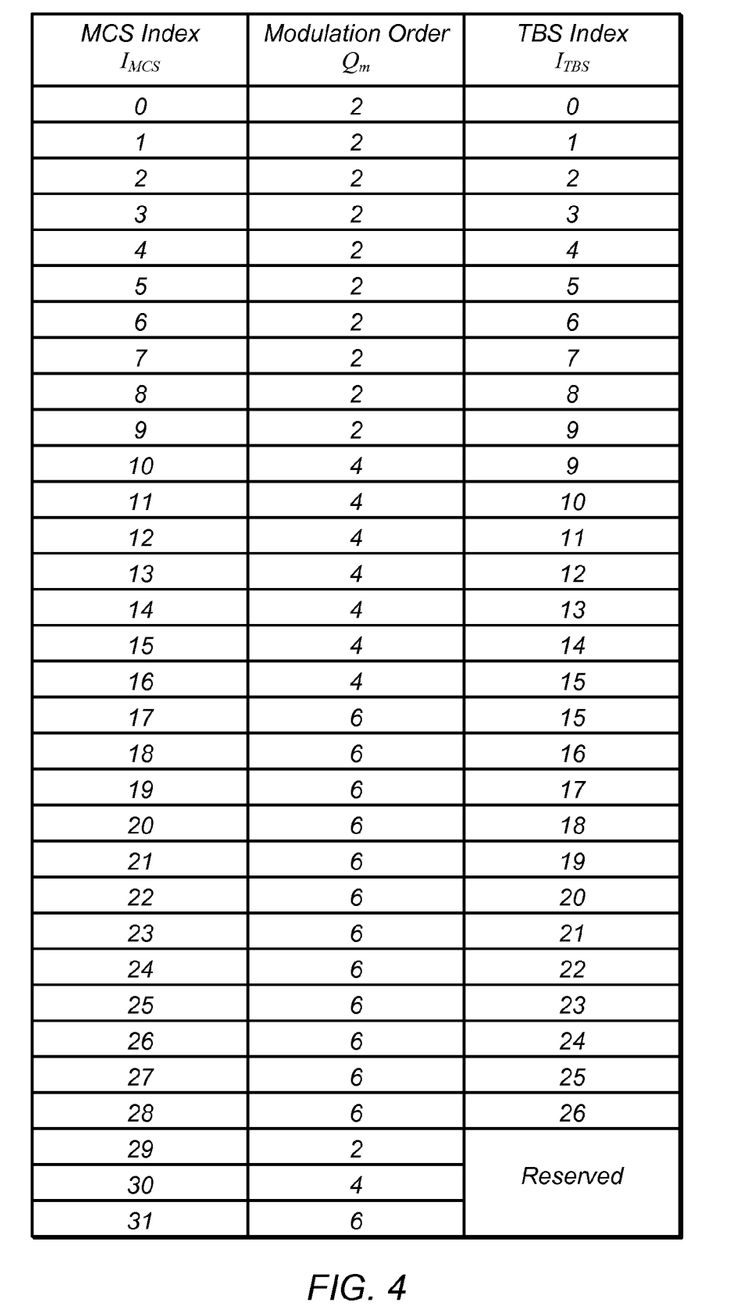
FIG. 4 illustrates an exemplary table of modulation and coding schemes which may be used in determining CQI values, according to one embodiment.

In LTE, the modulation and coding schemes (MCS) are defined to allow different levels of coding rates and modulation orders such as in the Table of FIG. 4 for DL physical downlink shared channel (PDSCH). The transport block size (TBS) index may be used in transport block size tables.

Based on the description of the CQI definition for LTE, from the UE perspective, the UE 106 may desire to achieve the 10% BLER target for any CQI given the DL configuration. Additionally, the scheduling algorithm in BS may be designed according to this UE requirement to increase throughput.

Note that what is proposed in LTE specification is one way of reporting and using CQI for optimizing the receiver throughput, which sets a fixed BLER target for the UE that can simplify the optimization at the BS. However, in order to further increase efficiency, adaptive BLER target can be used based on the UE channel conditions and network scenarios. Note that in the rest of the discussion, embodiments will be directed to those with the fixed BLER target for CQI, but the procedure can be generalized to varying BLER targets for CQI. Note that for MIMO transmissions, multiple hypotheses of the precoding matrices and rank selection (the number of spatial layers) can be tried by the UE to determine the optimal precoding matrix index (PMI) and rank indication (RI).

Figure 5:
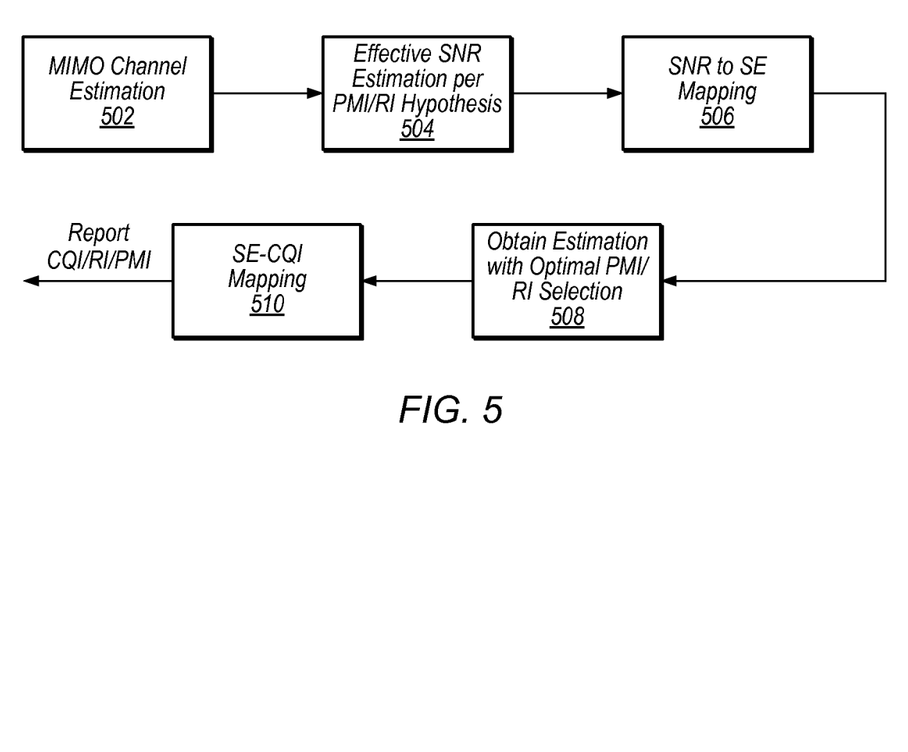
FIG. 5 illustrates an exemplary method for providing CSF report, according to one embodiment.

FIG. 5—Exemplary CQI Calculation

FIG. 5 illustrates embodiments of a method for generating channel quality indicators according to one embodiment. The method of FIG. 5 may generate a CQI that is based on the current conditions that is being experienced by the UE 106. The method shown in FIG. 5 may be used in conjunction with any of the computer systems or devices shown in the Figures, among other devices. In various embodiments, some of the method elements shown may be performed concurrently, in a different order than shown, or may be omitted. Additional method elements may also be performed as desired. As shown, the method of FIG. 7 may operate as follows.

In 502, MIMO channel estimation and/or noise estimation may be performed. In one embodiment, the channel estimation may be used to generate a whitened channel estimation matrix for CQI calculation.

In 504, effective SNR estimation per PMI/RI Hypothesis may be determined. In one embodiment, the SNR estimation may be based on the whitened channel estimation and the receiver algorithm. Generally speaking, there are several types of receiver demodulation algorithms including LMMSE (linear minimum mean square error), MLM (maximum likelihood method), and LMMSE-SIC (LMMSE with serial interference cancellation), among others.

In 506, the estimated SNR value may be mapped to an estimated spectral efficiency (SE) metric, e.g., using an SNR to SE mapping table. This mapping may be based on the channel capacity and possible loss due to practical receivers. Note that the SE estimation can be done in a finer granularity on a small number of resource blocks (e.g., two RBs). In one embodiment, the SE may be further processed, e.g., involving averaging across wideband, filtered over time, etc.

In 508, an estimation with the optimal PMI/RI (precoding matrix index/rank index) selection may be performed. The PMI/RI may be related to MIMO transmissions and may indicate the number of layers of transmission in MIMO scenarios. In one embodiment, the UE can use its channel estimation to determine the best PMI & RI and feedback to BS for it to apply at the BS side. In general, these values may be calculated along with CQIs, and conceptually, they are all part of CSF. In the context of LTE, the channel quality feedback may report CQI, PMI and RI separately.

In 510, SE to CQI mapping may be performed to determine the CQI, e.g., using an SE-CQI mapping table. As discussed above, the SE-CQI mapping table may be generated by an adaptive CQI method described in FIGS. 3 and 5. The SE-CQI mapping table may be selected based on the current communication scenario as noted above. The CQI and/or RI/PMI values may then be reported. Note that CQIs may include any of various channel quality feedback indications. For example, the term "CQI" may generally include RI/PMI values as well as the channel quality for BS to select a proper code rate (MCS). Thus, discussions above regarding CQI may include one or more values, including RI/PMI values. In this specific instance, the channel quality, RI, and PMI values are provided in the CSF.

Generally, filtering the SE may be important for CQI/PMI/RI reporting and may reflect how fast the UE responds to the channel or related spectral efficiency changes. In one embodiment, the filtering mechanisms may include FIR or IIR. FIR filtering generally has a fixed length of memory and is a weighted sum of previous SE estimation. An IIR filter generally has a memory of infinite length with the impact of each sample exponentially decreasing, which typically provides a smooth weighted average across the time. A simple IIR filter would be a single-pole IIR filter and the time constant can be approximated as the inverse of the IIR filter coefficient.

Furthermore, the CSF report requested by the BS may include a wide-band (WB) or M-subband report. The WB report may require the UE to report an averaged WB estimation of CQI. The M-subband CQI report mode specifies the UE to report the subband CQIs on M different subbands with a defined number of RBs (in LTE, each RB may contain 12 tones with 180 kHz bandwidth). In order to respond to different CQI report mode, the SE averaging or filtering may need to be performed in the frequency domain accordingly.

Doppler Estimation

In a dynamic propagation environment, Doppler estimation may be used to estimate the Doppler spread encountered by the UE as it moves with non-zero speed. Doppler spread is directly proportional to the channel time correlation. In other words, the faster the UE moves, the larger the Doppler spread encountered and smaller the channel correlation time. The information about how long a channel stays correlated may be critical for proper filtering and processing of channel and noise estimation and hence may have a direct impact on DL demodulation of traffic and control channels.

There are multiple ways to estimate Doppler spread, including:

1) Considering that the channel time auto-correlation has a direct relationship with the Doppler spread, instead of directly estimating the Doppler spread, a channel time auto-correlation estimate may be used to perform Doppler spread classification into various Doppler spread regimes.

2) Maximum likelihood estimation based on the Doppler power spectral density: The Doppler power spectral density (PSD) of a fading channel describes how much spectral broadening it causes. The UE can estimate its PSD using the channel estimation obtained from the pilot signals, and then estimate the Doppler shift based on maximum likelihood estimation of the expected Doppler PSD.

Adaptive CSF Report Under DRX Scenarios

The following sections relate to an adaptive CSF report algorithm for DRX. Since the CSF report is usually not required if the UE is in idle state, the following discussion primarily relates to the CSF report in C-DRX scenarios. However, the methods described herein may be used in any of various types of DRX modes, including idle mode.

The following are key parameters related to various embodiments of the algorithm discussed below:

1) Doppler shift estimation, $f_d$

2) DRX cycle length in milliseconds (or sleep period), $T_{DRX}$

3) CQI report offset in a CDRX cycle, $T_{offset}^{CQI}$

4) Channel estimation warm-up time, $T_{warmup}^{CE}$: The time it takes to have channel estimation to converge to an accurate estimation which is needed considering time and frequency domain filtering are usually applied in channel estimation algorithms to have stable and steady channel estimates based on pilot signals, or reference signals in the LTE context. Here the warm-up time also includes the warm-up time for spectral efficiency (SE) estimation, which also usually goes through a filtering structure to have stable SE estimates.

5) Other DRX wake-up overhead, $T_{warmup}^{overhead}$: Other DRX wake-up overhead such as the time it needs to allow the time-tracking loop, frequency tracking loop or automatic gain control loop to converge, etc. Note that the channel estimation warm-up can be in parallel with other wake-up overhead mentioned here.

6) Threshold, thresh: may be adjusted in various manners, as discussed below

Providing a CSF Report on an Early Subframe of CDRX on-Duration

In the following, the scenario is described where the CSF report is required or scheduled for an early subframe (e.g., the first subframe) during the CDRX on-duration. For these scenarios, in order to warm up the channel estimation and SE estimation, the UE 106 wakes up well before the CDRX on-duration (e.g., 7-11 or more milliseconds), which consumes a lot of power for the UE 106. This warm-up time is represented by $T_{warmup}^{CE}$. This extra wake-up time can be even comparable with the CDRX on-duration time length (e.g., 10 ms) to communicate a reasonable CSF report. Accordingly, in the following, the CSF calculated from previous DRX cycles may be leveraged (e.g., re-used or re-transmitted) under certain scenarios described below to save the extra wake-up time and/or improve the CSF report if there is a hardware/design constraint on how early the UE can be waken up before CDRX.

Figure 7:
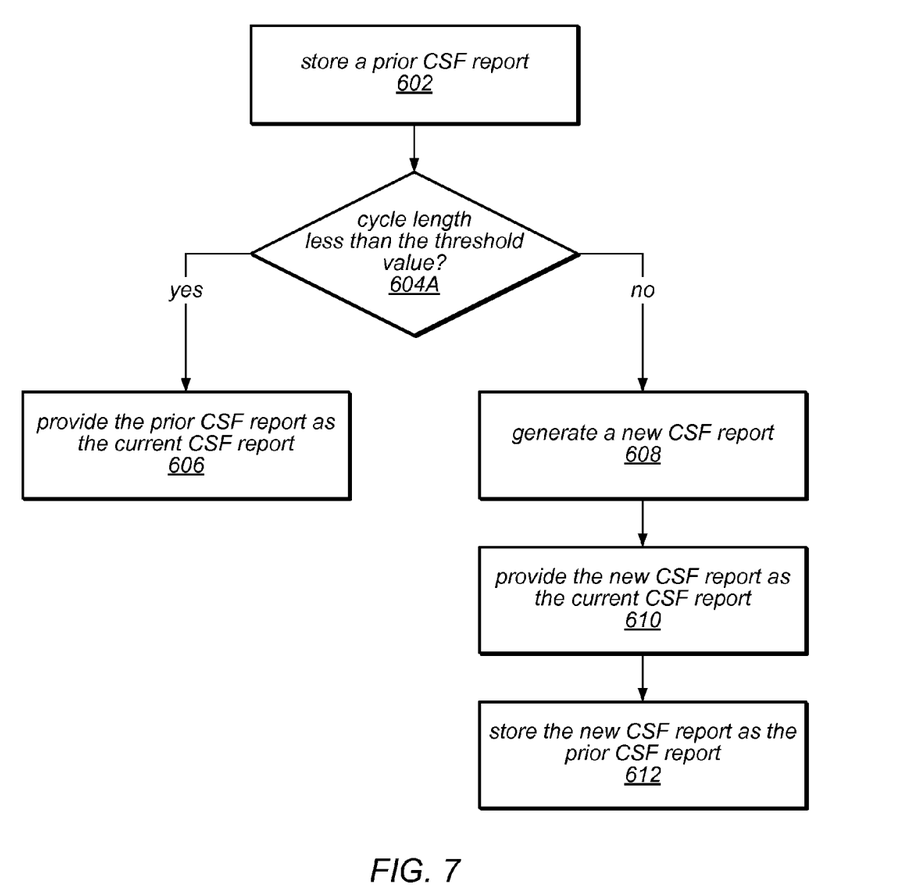

One example of the adaptive algorithm is described as below (also described in FIG. 7):

If $T_{DRX}$<thresh, the UE carries over or reuses the CSF values from the end of previous CDRX cycles. In these cases, the UE make wake up before the On-Duration by the length of time of $T_{warmup}^{overhead}$.

Otherwise, the UE wakes up earlier during the current CDRX cycles to start channel estimation and SE estimation for CSF calculation. The UE may wake up by the amount of time of $T_{warmup}^{CE}$. Note that $T_{warmup}^{CE}$ is generally several milliseconds longer than $T_{warmup}^{overhead}$.

The threshold, thresh, is introduced to allow:

1) The UE to restart the CSF report (generate a new CSF report) if the DRX cycle is long and the probability the channel varies dramatically is high;

2) The UE to reuse the CSF report from the previous DRX cycle when the DRX cycle length is within a reasonable range and where the calculated CSF from previous CDRX cycles still reflects the channel quality for current CDRX cycle.

In some embodiments, the above method may be adapted, e.g., dynamically, based on Doppler estimation. More specifically, the above algorithm can be further improved since the estimated Doppler value indicates the channel variation characteristics, which can be used to optimize the threshold, thresh.

For example, if the Doppler estimation is high (e.g., above a threshold), it may indicate that the UE 106 is moving quickly and the channel conditions the UE 106 experiences can vary dramatically. In such situations, it may be desirable to dynamically adjust the threshold, thresh, to a lower value. Alternatively, if the Doppler estimation is low (e.g., below a threshold), it may indicate that the UE 106 is stationary or moving slowly. In these channel conditions the UE 106 experiences vary slowly, allowing for a higher threshold value. Accordingly, the CSF can be carried over from previous CDRX cycle without a large performance impact, allowing for more efficient use of power.

Alternatively, or additionally, the method may be adapted based on other criteria, such as physical (PHY) layer key performance indicators (KPI) from previous cycles (e.g., previous CDRX cycles). Such criteria may be used since they are directly linked to the downlink performance. Exemplary criteria include throughput, error rate (e.g., downlink BLER), residual timing errors, and residual frequency errors. Metrics such as throughput and error rate can be directly used for considering the tradeoff between power optimization and throughput maximization. For example, if the error rate exceeds a threshold amount, a new CSF may need to be generated; otherwise, a previous CSF may be used. Similarly, if the throughput decreases by a threshold amount or falls below a threshold throughput level, a new CSF may need to be generated; otherwise, a previous CSF may be used. The physical layer KPI can also be used for adapting the thresh for optimizing the throughput and power consumption.

The decision of performing CSF carry-over (using a previous CSF) may be further determined by considering the tradeoff between the power consumption and performance. For example, in battery-limited applications or scenarios, CSF carryover can be applied given the constraint of the performance loss (measured by downlink packet loss ratio for example). In one embodiment, lower performance may be accepted (e.g., using a larger threshold value) as battery life decreases, or in battery sensitive conditions or scenarios. Thus, in each of the methods described in FIGS. 6-9 below, the method may increase the threshold value as battery life decreases, or may increase the threshold value in battery sensitive conditions or scenarios.

Figure 6:
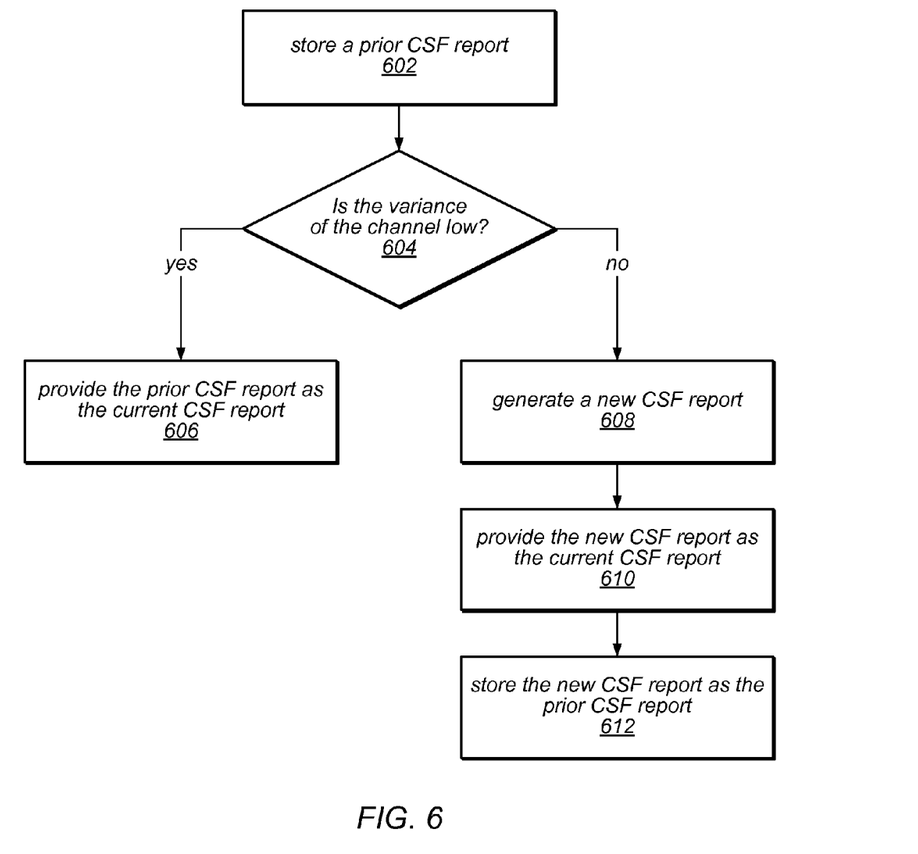
FIGS. 6-9 illustrate various methods for providing prior or new CSF reports.

FIG. 6—Using Prior CSF Reports Based on Channel Variance Estimation

FIG. 6 illustrates a method for using prior CSF reports based on a determination of variance in the channel. The method shown in FIG. 6 may be used in conjunction with any of the computer systems or devices shown in the above Figures, among other devices. For example, the method of FIG. 6 may be performed by UE 106. In various embodiments, some of the method elements shown may be performed concurrently, in a different order than shown, or may be omitted. Additional method elements may also be performed as desired. As shown, this method may operate as follows.

In 602, a prior CSF report may be stored by UE device 106. The prior CSF report may be from a prior DRX cycle, e.g., an immediately prior DRX cycle or earlier, as desired. The DRX cycle may be related to communication between the UE device 106 and a BS.

In 604, the UE device 106 estimates whether the variance of the channel is low. Step 604 may be performed in any of various ways.

For example, the UE device 106 may estimate the variance of the channel by comparing a cycle length of the DRX to a threshold value. If the cycle length of the DRX is less than the threshold value then the estimate of the variance of the channel is deemed to be low. If the cycle length of the DRX is greater than the threshold value then the estimate of the variance of the channel is determined to be not low (e.g., high). The UE device 106 may be configured to determine if the UE device 106 is moving or stationary and may adjust the threshold value based on whether the UE device 106 is determined to be moving or stationary. This method is described in greater detail below with respect to FIG. 7.

Alternatively, the UE device 106 may estimate the variance of the channel by comparing a connection characteristic to a threshold value. If the connection characteristic does not pass the threshold value then the estimate of the variance of the channel is determined to be low. If the connection characteristic does pass the threshold value then the estimate of the variance of the channel is determined to be not low (e.g., high). The connection characteristic may comprise parameters such as error rate, throughput, etc. This method is described in greater detail below with respect to FIG. 8.

As another alternative, the UE device 106 may estimate the variance of the channel by determining whether the UE device 106 is moving or stationary. This may be determined by determining a current Doppler shift that exists on the channel, and comparing the determined Doppler shift to a threshold. If the UE device 106 is determined to be stationary (the amount of Doppler shift is below the threshold) then the estimate of the variance of the channel is determined to be low. If the UE device is determined to be moving (the amount of Doppler shift is above the threshold) then the estimate of the variance of the channel is determined to be not low (e.g., high).

In 606, if the estimate of the variance of the channel is low, the prior CSF report may be provided as the current CSF report. For example, where the channel is not varying by very much, or where the channel has not varied much since the last CSF report, the prior CSF report may still be valid, thereby saving power by eliminating the need to wake up early to warm-up and generate a new CSF report. The CSF report may be provided to a BS in communication with the device.

In 608, if the estimate of the variance of the channel is not low, a new CSF report may be generated. In this case, the device may need to wake up well before the DRX on-duration, e.g., in order to warm-up circuits to generate an accurate CSF report.

In 610, the new CSF report may be provided as the current CSF report. Similar to 606 above, the CSF report may be provided to the BS.

In 612, the new CSF report may be stored as the prior CSF report. The older prior CSF, from 602, may be overwritten by the new CSF report. Alternatively, they both may be stored by the device, e.g., for time series analysis.

The method of FIG. 6 may be performed multiple times, e.g., for each DRX cycle. Additionally, note that the method of FIG. 6 may apply to embodiments where the CSF report is required early in the cycle (e.g., at the first sub-frame of the cycle). Where the CSF report is required at a later point in the cycle, the method of FIG. 6 may be augmented with the method shown in FIG. 9.

FIG. 7—Using Prior CSF Reports Based on Cycle Length

FIG. 7 illustrates one embodiment of a method for using prior CSF reports based on cycle length. The method shown in FIG. 7 may be used in conjunction with any of the computer systems or devices shown in the above Figures, among other devices. For example, the method of FIG. 7 may be performed by UE 106. In various embodiments, some of the method elements shown may be performed concurrently, in a different order than shown, or may be omitted. Additional method elements may also be performed as desired. As shown, this method may operate as follows.

In 602, a prior CSF report may be stored by a device. The prior CSF report may be from a prior DRX cycle, e.g., an immediately prior DRX cycle or earlier, as desired. The DRX cycle may be related to communication between the device and a BS.

In 604A, the cycle length of the DRX may be compared to a threshold value.

In 606, if the cycle length is less than the threshold value, the prior CSF report may be provided as the current CSF report. For example, for shorter cycle lengths, the prior CSF report may still be valid, thereby saving power by eliminating the need to wake up early to warm-up and generate a new CSF report. The CSF report may be provided to a BS in communication with the device.

In 608, if the cycle length is greater than the threshold value, a new CSF report may be generated. In this case, the device may need to wake up well before the DRX on-duration, e.g., in order to warm-up circuits to generate an accurate CSF report.

In 610, the new CSF report may be provided as the current CSF report. Similar to 606 above, the CSF report may be provided to the BS.

In 612, the new CSF report may be stored as the prior CSF report. In one embodiment, the older prior CSF, from 602, may be overwritten by the new CSF report. Alternatively, they both may be stored by the device, e.g., for time series analysis.

The method may further include modifying the threshold value. For example, as discussed above, the method may include determining Doppler shift information and using the Doppler shift information to adjust the threshold value. The threshold value may be modified at various different intervals. For example, the threshold value may be modified every cycle, every nth cycle, multiple times in a cycle, etc. Alternatively, or additionally, the threshold value may be modified whenever there are changes to the measured Doppler shift, e.g., when a new Doppler shift is measured that is significantly different than a previous Doppler shift, the threshold value may be changed. In one embodiment, higher Doppler shifts may result in lower threshold values and lower Doppler shifts may result in higher threshold values.

Finally, the method of FIG. 7 may be performed multiple times, e.g., for each DRX cycle. Additionally, note that the method of FIG. 7 may apply to embodiments where the CSF report is required early in the cycle (e.g., at the first sub-frame of the cycle). Where the CSF report is required at a later point in the cycle, the method of FIG. 7 may be augmented with embodiments described below, e.g., related to the method shown in FIG. 9.

Figure 8:
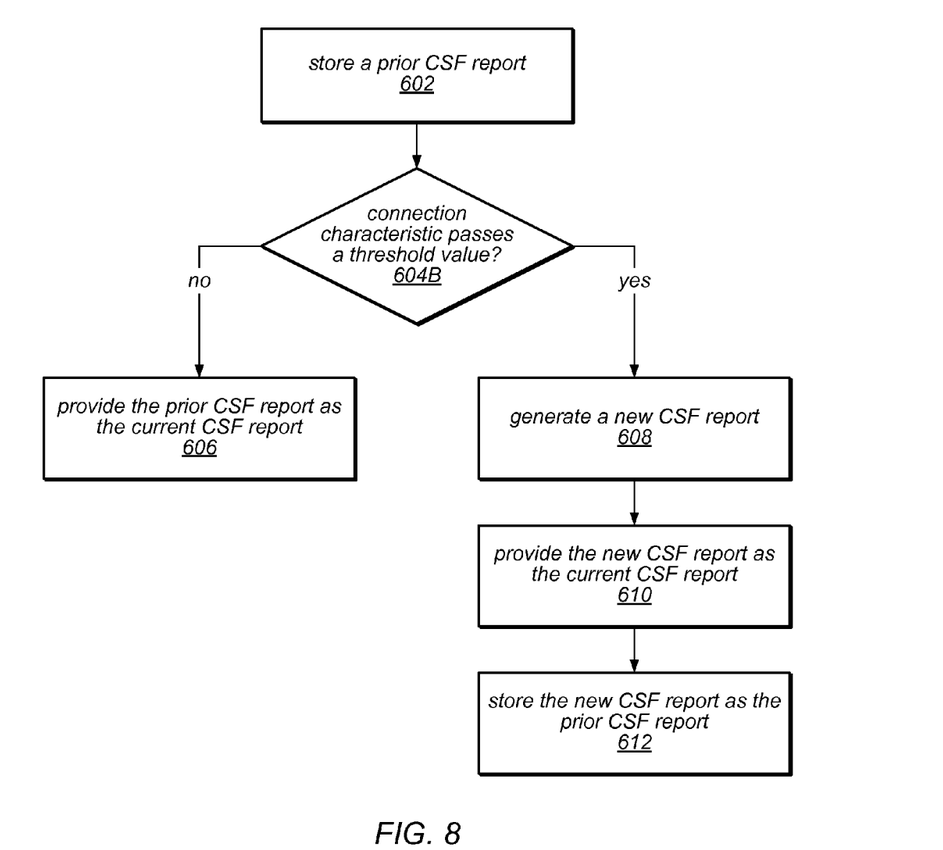

FIG. 8—Using Prior CSF Reports Based on Connection Characteristics

FIG. 8 illustrates one embodiment of a method for using prior CSF reports based on connection characteristics. The method shown in FIG. 8 may be used in conjunction with any of the computer systems or devices shown in the above Figures, among other devices. For example, the method of FIG. 8 may be performed by UE 106. In various embodiments, some of the method elements shown may be performed concurrently, in a different order than shown, or may be omitted. Additional method elements may also be performed as desired. As shown, this method may operate as follows.

In 602, a prior CSF report may be stored by a device. The prior CSF report may be from a prior DRX cycle, e.g., an immediately prior DRX cycle or earlier, as desired. The DRX cycle may be related to communication between the device and a BS.

In 604B, a connection characteristic may be compared to a threshold value. The current connection characteristic may be similar to the criteria discussed above, e.g., the KPI of previous cycles (e.g., an immediately prior cycle), ones measured in the current cycle, etc. Two exemplary characteristics include error rate and throughput. For example, the method may determine if the error rate exceeds an error rate threshold value (e.g., 10%). Alternatively, or additionally, the method may determine if the throughput falls below a throughput threshold value. In further embodiments, the method may determine if a decrease in throughput exceeds a decrease in throughput threshold value. Similar descriptions correspond to other connection characteristics.

If the current connection characteristic does not pass the threshold value, in 606 the prior CSF report may be provided as the current CSF report. The CSF report may be provided to a BS in communication with the device. For example, where the error rate is below the error rate threshold, the prior CSF report may be provided. Alternatively, or additionally, where the throughput stays above the throughput threshold value, the prior CSF report may be provided. Similarly, where the throughput does not decrease by a threshold amount, the CSF report may be provided. Similar descriptions correspond to other connection characteristics.

If the current connection characteristic does pass the threshold value, in 608 a new CSF report may be generated. These cases may be the opposite of those listed in 606 above.

In 610, the new CSF report may be provided as the current CSF report. Similar to 606 above, the CSF report may be provided to the BS.

In 612, the new CSF report may be stored as the prior CSF report. In one embodiment, the older prior CSF, from 602, may be overwritten by the new CSF report. Alternatively, they both may be stored by the device, e.g., for time series analysis.

Finally, the method of FIG. 8 may be performed multiple times, e.g., for each DRX cycle. Additionally, note that the method of FIG. 8 may apply to embodiments of FIG. 6, 7 and/or FIG. 8, discussed below. Thus, any of the described methods may be combined, e.g., to be used in the same device.

Providing a CSF Report on Later Subframes of CDRX on-Duration

In the following, the scenario where the CSF report is required or scheduled for a later subframe during the CDRX on-duration is described. The following provides an exemplary algorithm:

If $T_{warmup}^{CE} \leq T_{offset}^{CQI} + T_{warmup}^{overhead}$, restart the CSF report calculation for current DRX cycle;

Else, resume spectral efficiency (SE) values from previous CDRX cycles, based on which the UE 106 calculates CSF values to be reported in current CDRX cycle. Or, if the CSF report format is the same as the previous CDRX cycle, the same CSF values from previous CDRX cycles can be reused.

The algorithm above indicates that if the time it takes to have stable CSF values is less than the time before the CSF report is required (including the overhead warm-up period, since that is required each period and can be used for CE warm-up), the UE 106 can determine a current CSF for current DRX cycle without the power penalty of early wake-up to prepare the receiver for good CSF reports.

Where that condition is not available, previous values may be used. In one embodiment, the adaptive algorithm for determining whether to use prior CSF reports (discussed above) may be used in such conditions. Alternatively, or additionally, even in the scenarios that the above condition is not satisfied, simulation or empirical performance results can be evaluated to allow tradeoff between the performance and the power consumption to allow a CSF report though it may not be fully converged and stabilized.

Moreover, if CSF reports are required for multiple subframes across the threshold of $T_{offset}^{CQI} + T_{warmup}^{overhead}$, the UE can adaptively switch from the carried-over CSF to the newly calculated CSF when it is stable enough.

Figure 9:
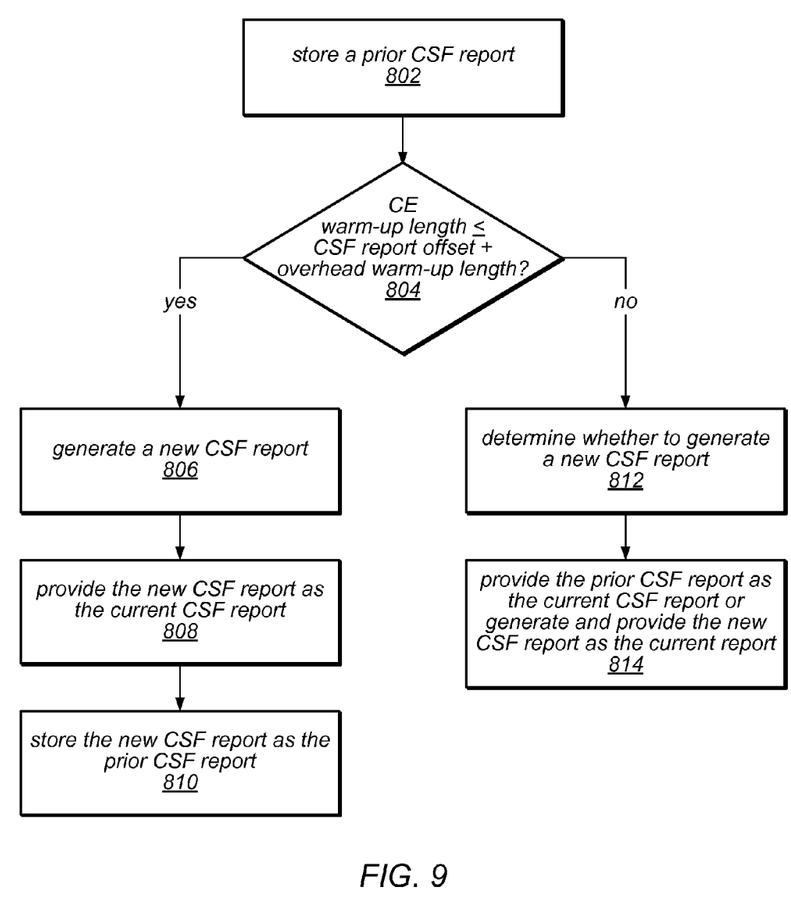

FIG. 9—Using Prior CSF Reports Based on CSF Report Offset

FIG. 9 illustrates one embodiment of a method for using prior CSF reports based on a CSF report offset. The method shown in FIG. 9 may be used in conjunction with any of the computer systems or devices shown in the above Figures, among other devices. For example, the method of FIG. 9 may be performed by UE 106. In various embodiments, some of the method elements shown may be performed concurrently, in a different order than shown, or may be omitted. Additional method elements may also be performed as desired. As shown, this method may operate as follows.

In 802, similar to 602 above, a prior CSF report may be stored by the UE device 106. The prior CSF report may be from a prior DRX cycle, e.g., an immediately prior DRX cycle or earlier, as desired. The DRX cycle may be related to communication between the device and a BS.

In 804, the channel estimation warm-up length may be compared to the CSF report offset added to the overhead warm-up length, similar to embodiments discussed immediately above.

In 806, if the channel estimation warm-up length is less than or equal to the CSF report offset added to the overhead warm-up length, a new CSF report may be generated.

Correspondingly, in 808, the new CSF report may be provided as the current CSF report, e.g., to the BS.

In 810, the new CSF report may be stored as the prior CSF report. In one embodiment, the previous prior CSF, from 802, may be overwritten by the new CSF report. Alternatively, they both may be stored by the device, e.g., for time series analysis.

In 812, if the channel estimation warm-up length is greater than the CSF report offset added to the overhead warm-up length, the method may determine whether to generate a new CSF report. For example, the methods described above, e.g., related to FIGS. 6 and 7, may be used to determine whether to generate the new CSF report. Alternatively, instead of performing additional analysis, a new CSF report may be generated (e.g., requiring the device to wake-up earlier than would be required by only the overhead warm-up amount, as opposed to in 806, where waking up earlier may not be required).

In 814, the prior CSF report may be provided as the current CSF report or a new CSF report may be generated and provided as the current CSF report, depending on the determination in 812 above.

Finally, the method of FIG. 9 may be performed multiple times, e.g., for each DRX cycle. Additionally, note that the method of FIG. 9 may apply to embodiments of FIG. 6, 7 and/or FIG. 8, discussed above. Thus, any of the described methods may be combined, e.g., to be used in the same device.

Further Embodiments

Note that in the present description, various embodiments are described in the context of LTE (Long-term evolution of UTMS). However, it is noted that the methods described herein can be generalized for CSF reporting using other wireless technologies and are not limited to the specific descriptions provided above.

Embodiments of the present invention may be realized in any of various forms. For example, in some embodiments, the present invention may be realized as a computer-implemented method, a computer-readable memory medium, or a computer system. In other embodiments, the present invention may be realized using one or more custom-designed hardware devices such as ASICs. In other embodiments, the present invention may be realized using one or more programmable hardware elements such as FPGAs.

In some embodiments, a non-transitory computer-readable memory medium may be configured so that it stores program instructions and/or data, where the program instructions, if executed by a computer system, cause the computer system to perform a method, e.g., any of a method embodiments described herein, or, any combination of the method embodiments described herein, or, any subset of any of the method embodiments described herein, or, any combination of such subsets.

In some embodiments, a device (e.g., a UE) may be configured to include a processor (or a set of processors) and a memory medium, where the memory medium stores program instructions, where the processor is configured to read and execute the program instructions from the memory medium, where the program instructions are executable to implement any of the various method embodiments described herein (or, any combination of the method embodiments described herein, or, any subset of any of the method embodiments described herein, or, any combination of such subsets). The device may be realized in any of various forms.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A user equipment (UE) device, the UE device comprising:
    an antenna for performing wireless communications with a base station (BS) over a channel;
    a memory for storing one or more channel state feedback (CSF) reports;
    wherein the UE device is configured to:
        store a CSF report from a previous cycle in which the UE device is in a low power mode;
        compare a cycle length for a current cycle to a threshold value; and
        in response to the cycle length being less than the threshold value, provide the CSF report from the previous cycle to the BS.

2. The UE device of claim 1, wherein when the cycle length is greater than the threshold value, the UE device is further configured to:
    generate a new CSF report; and
    provide the new CSF report to the BS.

3. The UE device of claim 1, wherein the UE device is further configured to estimate a variance of the channel by comparing the cycle length to the threshold value.

4. The UE device of claim 1, wherein the UE device is configured to determine if the UE device is moving or stationary;
wherein the UE device is configured to adjust the threshold value based on whether the UE device is determined to be moving or stationary.

5. The UE device of claim 4, wherein the UE device is configured to determine whether the UE device is moving or stationary by using Doppler shift estimation.

6. The UE device of claim 1, wherein the UE device is configured, in response to the cycle length being less than the threshold value, to determine that the stored CSF report from the previous cycle reflects a channel quality for the channel for the current cycle.

7. A method for providing a channel state feedback (CSF) report by a user equipment (UE) device, the method comprising:
the UE device performing:
storing a prior CSF report from a previous cycle in which the UE device is in a low power mode;
comparing a cycle length for a current cycle to a threshold value; and
in response to the cycle length being less than the threshold value, providing, to a base station, the prior CSF report from the previous cycle.

8. The method of claim 7, further comprising the UE device performing:
subsequent to providing the prior CSF report from the previous cycle for the current cycle, comparing a different cycle length for a different cycle to the threshold value;
in response to the different cycle length being greater than the threshold value, generating a new CSF report;
providing to the base station the new CSF report; and
storing the new CSF report as the prior CSF report.

9. The method of claim 7, wherein the low power mode is a discontinuous reception mode.

10. The method of claim 7, further comprising:
determining if the UE device is moving or stationary; and
adjusting the threshold value based on whether the UE device is determined to be moving or stationary.

11. The method of claim 10, wherein said determining whether the UE device is moving or station comprises determining a current Doppler shift using Doppler shift estimation.

12. The method of claim 11, wherein said adjusting comprises decreasing the threshold value for higher Doppler shift values and increasing the threshold value for lower Doppler shift values.

13. The method of claim 7, wherein said providing the prior CSF report is performed at a first sub-frame of an on-duration cycle of the UE device.

14. A non-transitory computer readable storage medium storing program instructions, that, when executed by one or more processors of a user equipment (UE) device, cause the one or more processors to carry out operations comprising:
storing channel state information from a prior reception cycle;
comparing a cycle length for a current reception cycle to a threshold value; and
in response to the cycle length being less than the threshold value, providing the channel state information from the prior reception cycle to a base station (BS).

15. The non-transitory, computer readable storage medium of claim 14, wherein the operations further comprise:
in response to the cycle length being greater than the threshold value, generating new channel state information;
providing the new channel state information to the BS; and
storing the new channel state information as the channel state information.

16. The non-transitory, computer readable storage medium of claim 14, wherein the operations further comprise estimating a variance of a channel to the BS by comparing the cycle length for the current reception cycle to the threshold value.

17. The non-transitory, computer readable storage medium of claim 14, wherein the operations further comprise:
determining whether the UE device is moving; and
in response to determining that the UE device is moving, adjusting the threshold value.

18. The non-transitory, computer readable storage medium of claim 14, wherein the operations further comprise determining whether the UE device is moving or stationary by using Doppler shift estimation.

19. The non-transitory, computer readable storage medium of claim 14, wherein the operations further comprise, in response to the cycle length being less than the threshold value, determining that the stored channel state information from the prior reception cycle reflects a channel quality for a channel between the BS and the UE for the current reception cycle.

20. The non-transitory, computer readable storage medium of claim 14, wherein the program instructions cause the one or more processors to provide the channel state information from the prior reception cycle to the BS during a first sub-frame of an on-duration cycle of the UE device.

* * * * *